US007499555B1

(12) United States Patent
Isvan

(10) Patent No.: US 7,499,555 B1
(45) Date of Patent: Mar. 3, 2009

(54) PERSONAL COMMUNICATION METHOD AND APPARATUS WITH ACOUSTIC STRAY FIELD CANCELLATION

(75) Inventor: Osman K. Isvan, Aptos, CA (US)

(73) Assignee: Plantronics, Inc., Santa Crux, CA (US)

( * ) Notice: Subject to any disclaimer, the term of this patent is extended or adjusted under 35 U.S.C. 154(b) by 1043 days.

(21) Appl. No.: 10/308,810

(22) Filed: Dec. 2, 2002

(51) Int. Cl.
*A61F 11/06* (2006.01)
*G10K 11/16* (2006.01)
*H03B 29/00* (2006.01)

(52) U.S. Cl. ..................... 381/71.6; 381/71.7; 381/182; 381/186; 381/380

(58) Field of Classification Search ................... 381/89, 381/182, 345, 380, 71.7, 71.6, 370, 372, 381/186, 349, 328, 335, 351; 181/148, 155, 181/156; 455/569.1
See application file for complete search history.

(56) References Cited

U.S. PATENT DOCUMENTS

| | | | | | |
|---|---|---|---|---|---|
| 4,549,631 | A | * | 10/1985 | Bose | 181/155 |
| 4,917,504 | A | | 4/1990 | Scott et al. | |
| 5,073,945 | A | * | 12/1991 | Kageyama et al. | 381/89 |
| 5,121,433 | A | * | 6/1992 | Kendall et al. | 381/1 |
| 5,134,659 | A | * | 7/1992 | Moseley | 381/72 |
| 5,561,717 | A | * | 10/1996 | Lamm | 381/89 |
| 5,588,065 | A | * | 12/1996 | Tanaka et al. | 381/96 |
| 5,675,658 | A | * | 10/1997 | Brittain | 381/72 |

(Continued)

FOREIGN PATENT DOCUMENTS

| | | |
|---|---|---|
| GB | 233 008 | 5/1925 |
| WO | WO 95/34184 | 12/1995 |

*Primary Examiner*—Vivian Chin
*Assistant Examiner*—Jason R Kurr
(74) *Attorney, Agent, or Firm*—Francois de Villiers; Michael D. Rodriguez

(57) ABSTRACT

Personal communication method and apparatus, such as telephone handsets and headsets, with acoustic stray field cancellation are disclosed. The personal communications device employs an echo canceling receiver generally including two displacement sources that are not in phase formed by at least one driver, an acoustic cavity corresponding to each displacement source, and an acoustic output port corresponding to and in acoustic connection with each displacement source via the corresponding acoustic cavity such that the acoustic length between the acoustic centers of the two ports is less than the distance between the acoustic center of each port and the acoustic center of the corresponding displacement source to which the port is acoustically connected. In another embodiment, the ports may be such that both ports are located on a same side of a surface of at least one of the displacement sources. As an example, the personal listening device may have at least two ports and a dedicated driver acoustically coupled to each port. The personal communication device may further include a transmit module. The ports may be driven and tuned such that when the device is worn, the ratio of acoustic pressure at a first location, e.g., the ear, to acoustic pressure at a second location, e.g. the transmit module, is substantially greater than that with either port acting alone. In another embodiment, the receiver ports are driven and tuned such that when the device is worn, the ratio of acoustic pressure at the first location to sound pressure gradient in a given direction at the second location is substantially greater than that with either port acting alone. The receiver thus achieves echo canceling for high frequencies.

16 Claims, 6 Drawing Sheets

U.S. PATENT DOCUMENTS

| | | | | |
|---|---|---|---|---|
| 5,721,401 | A * | 2/1998 | Sim | 181/148 |
| 5,790,679 | A * | 8/1998 | Hawker et al. | 381/163 |
| 5,809,156 | A * | 9/1998 | Bartels et al. | 381/370 |
| 5,933,506 | A * | 8/1999 | Aoki et al. | 381/151 |
| 6,002,949 | A | 12/1999 | Hawker et al. | |
| 6,144,738 | A | 11/2000 | Hawker et al. | |
| 6,259,796 | B1 * | 7/2001 | Lin | 381/371 |
| 6,301,367 | B1 | 10/2001 | Boyden et al. | |
| 6,307,943 | B1 | 10/2001 | Yamagishi | |
| 6,324,284 | B1 | 11/2001 | Hawker et al. | |
| 6,628,790 | B1 * | 9/2003 | Klein | 381/89 |
| 7,103,193 | B2 * | 9/2006 | Croft, III | 381/345 |

* cited by examiner

PERSONAL COMMUNICATION METHOD AND APPARATUS WITH ACOUSTIC STRAY FIELD CANCELLATION

BACKGROUND OF THE INVENTION

1. Field of the Invention

The present invention relates generally to personal communication devices. More specifically, personal communication method and apparatus, such as telephone handsets and headsets, with acoustic stray field cancellation are disclosed.

2. Description of Related Art

In personal communication devices such as telephone handsets and headsets, acoustic coupling between the receiver module (the speaker) and the transmit module (the microphone) results in some of the received signals appearing in the transmit path. Where the transmission delay (latency) is sufficiently long, such acoustic coupling between the speaker and the microphone causes the far-end talker to hear an annoying echo of his/her own voice. Thus, communication devices used in time-delayed networks, such as Voice over Internet Protocol (VoIP), should provide high levels of signal loss between the receive and transmit modules in order to minimize acoustic coupling.

In addition, speakers in telephone headsets or handsets should ideally produce low sound levels in the far field (stray field) in order so as to increase the level of privacy in the communication.

However, the electro-acoustic sensitivity of the receive and transmit modules of a headset typically must meet certain system requirements. In particular, the International Telecommunications Union, in combination with other international and national standards for telecommunications equipment, specifies values for electro-acoustic losses Relative Receive Loudness Rating (RRLR) and Relative Send Loudness Rating (RSLR), respectively, to ensure that when two people communicate via telephone (i.e., over a reduced frequency band), the acoustic loss from the mouth of the talker to the ear of the listener is the same as a face-to-face communication, as far as loudness is concerned. Loudness refers to the hearing sensation produced by an acoustic stimulus. Specifically, the RRLR and RSLR are specified to be 0 dB and 8 dB, respectively, in terms of loss relative to a specified Independent Reference System (IRS). The electro-acoustic loss RRLR represents the frequency-weighted average receive sensitivity of a telephone headset and is the ratio of the sound pressure at the user's ear drum reference point, DRP, to the voltage at the headset receive terminals. Similarly, the electro-acoustic loss RSLR represents the frequency-weighted average transmit sensitivity of a telephone headset and is the ratio of the voltage at the transmit terminals of the headset to the sound pressure at the user's mouth reference point, MRP.

Some personal communication devices have a relatively large distance between the microphone and the user's mouth and a reduced distance between the speaker and microphone. Examples of such devices include small cell phones and boomless headsets. Such a personal communication device should have a relatively more sensitive microphone and/or greater amplification in order to compensate for the larger distance between the microphone and the user's mouth. However, the reduced distance between the speaker and microphone results in increased acoustic coupling in the acoustic cross talk path. Thus, locating the microphone further away from the talker's mouth undesirably decreases the echo return loss at the telephone/network interface.

The echo return loss in a communication device is a function of frequency. A frequency-weighted average signal power loss between the electrical receive and transmit terminals of a communications headset is characterized by HCLw (Headset Coupling Loss, weighted). HCLw normalized with respect to RRLR and RSLR is referred to as Relative Terminal Coupling Loss, weighted (RTCLw).

Thus, it is desirable to achieve an ideal combination of receive sensitivity, transmit sensitivity, and receive-to-transmit coupling loss (HCLw) while at the same time maximizing RTCLw to provide full duplex telephone communication with high audio quality, particularly for boomless communication headsets and cell phones.

Conventional ear cups with an acoustic seal behind the speaker diaphragm and soft ear cushions on the face plate have been implemented to maximize the acoustic coupling to the user's ear and provide some of the desired properties such as reduced RRLR (loss) and increased HCLw. However, these headsets are relatively bulky and heavy and require headbands. In addition, although the use of noise canceling microphones especially with long microphone booms helps reduce RSLR (loss) and increase HCLw, the echo return loss performance achieved for headsets with short booms and boomless headsets are generally insufficient for digital networks.

Some conventional boomless headsets have decreased receive sensitivity and/or the transmit sensitivity below the recommended levels. As a result, these headsets do not provide satisfactory performance in noisy environments. One method to overcome this drawback is the use of form-fitting ear inserts on "ear bud" type headphones to create an acoustic seal between the receiver and the user's ear. Although such headphones increase acoustic isolation as well as receive sensitivity, such form-fitting ear inserts on ear bud type headphones are uncomfortable for some users.

Many ear bud and on-the-ear headsets and headphones have a rear opening or port to provide a vent for the backside of the speaker diaphragm. FIG. 1 is a cross-sectional view of an exemplary conventional headset receiver 20 shown in relation to a user's ear 40. The headset receiver 20 may be employed in an ear bud or on-the-ear headset or headphone. As shown, the headset receiver 20 includes an outer casing 22 defining a front port 24 and a rear port 26. The front port 24 is located on the headset receiver 20 such that when the receiver is placed in the user's ear 40, the front port 24 is positioned adjacent or otherwise near the ear canal 42 of the ear 40. The headset receiver 20 further includes a diaphragm 28 driven by a voice coil 30 and a magnet 32. The diaphragm 28, supported by a front plate 34, divides the volume defined by the outer casing 22 into a front cavity 44 and a rear cavity 46. The front plate 34 and a back plate 36 are used to complete the magnetic circuit and used to direct the magnetic field to a focal point in a gap formed by the front plate 34 and a pole piece 38.

The rear port 26 in the exemplary conventional headset receiver 20 is provided to increase the low frequency response of the receiver 20. The rear port 26 also provides an added side benefit in that the acoustic output of the rear port 26, which is out of phase with the front port 24, results in acoustic cancellation generally in the far field (stray field) and specifically at a transmit microphone, thereby improving the echo path loss. However, as is typical with conventional headsets, the acoustic cancellation achieved by the rear port 26 is effective only at low frequencies. The acoustic cancellation diminishes at mid-frequencies and becomes a detriment at high frequencies when the acoustic outputs of the front and rear ports 24, 26 cause constructive interference as will be further described in the detailed description of the invention. The upper curve of the graph of FIG. 2 illustrates the echo frequency response of an exemplary conventional boomless headset with a rear port.

As is shown, although the echo level of a typical conventional headset with a rear port is low at low frequencies, the echo level rises steeply with increased frequency.

Two conventional solutions to attempt to resolve the problem of diminishing acoustic cancellation at higher frequencies are voice switching and voice expansion employing signal compression in the transmit channel. In both voice switching and voice expansion, the transmit gain is a function of the transmit signal level. In voice switching, the transmit gain is switched between a high state (when the user is talking) and a low state (when the user is not talking). In voice expansion, the transmit gain is adjusted infinitesimally between two limits with appropriate attack and release time constants so that there are no audible steps in the transmitted background noise level. Voice switching and voice expansion systems are developed primarily to suppress background noise, but with well-optimized voice expansion circuits in a quiet environment, up to 12 dB increase in echo path loss can be achieved with no audible artifact. However, voice expansion alone is insufficient for boomless headsets and the effectiveness of voice expansion is further diminished in noisy environments.

Another example of a conventional solution that attempts to resolve the problem of diminishing acoustic echo cancellation at higher frequencies is electronic echo cancellation with digital signal processing. In particular, an echo canceller adaptively predicts the echo signal and removes the predicted echo signal from the transmit path. However, such a method adds even more delay, is expensive to implement, consumes power, and can generate audible artifacts.

Thus, as the echo levels resulting from acoustic coupling in boomless and short-boom headsets can be high, it is desirable to provide electronic echo reduction for a communications headset used in digital networks with packet delay to ensure acceptable echo performance.

SUMMARY OF THE INVENTION

Personal communication method and apparatus, such as telephone handsets and headsets, with acoustic stray field cancellation are disclosed. In particular, an acoustic echo-canceling headset provides acoustic stray field cancellation to improve the echo path loss. It should be appreciated that the present invention can be implemented in numerous ways, including as a process, an apparatus, a system, a device, or a method. Several inventive embodiments of the present invention are described below.

The personal communications device employs an echo canceling receiver generally including two displacement sources that are not in phase (phase shifted) formed by at least one driver, an acoustic cavity corresponding to each displacement source, and an acoustic output port corresponding to and in acoustic connection with each displacement source via the corresponding acoustic cavity such that the acoustic length between the acoustic centers of the two ports is less than the distance between the acoustic center of each port and the acoustic center of the corresponding displacement source to which the port is acoustically connected. In another embodiment, the ports may be such that both ports are located on a same side of a surface of at least one of the displacement sources. As an example, the personal listening device may have at least two ports and a dedicated driver acoustically coupled to each port. The personal communication device may further include a transmit module. The ports may be driven and tuned such that when the device is worn, the ratio of acoustic pressure at a first location, e.g., the ear, to acoustic pressure at a second location, e.g. the transmit module, is substantially greater than that with either port acting alone. In another embodiment, the receiver ports are driven and tuned such that when the device is worn, the ratio of acoustic pressure at the first location to sound pressure gradient in a given direction at the second location is substantially greater than that with either port acting alone.

The acoustic echo canceling headset receiver not only increases echo path loss (i.e., terminal coupling loss) but also provides nearly flat echo frequency response, higher listening volume without squealing, possibility of shorter microphone booms, reduced complexity of necessary electronic echo control, and/or improved privacy with received signals.

These and other features and advantages of the present invention will be presented in more detail in the following detailed description and the accompanying figures which illustrate by way of example the principles of the invention.

BRIEF DESCRIPTION OF THE DRAWINGS

The present invention will be readily understood by the following detailed description in conjunction with the accompanying drawings, wherein like reference numerals designate like structural elements, and in which.

DESCRIPTION OF SPECIFIC EMBODIMENTS

Personal communication method and apparatus, such as telephone handsets and headsets, with acoustic stray field cancellation are disclosed. The following description is presented to enable any person skilled in the art to make and use the invention. Descriptions of specific embodiments and applications are provided only as examples and various modifications will be readily apparent to those skilled in the art. The general principles defined herein may be applied to other embodiments and applications without departing from the spirit and scope of the invention. Thus, the present invention is to be accorded the widest scope encompassing numerous alternatives, modifications and equivalents consistent with the principles and features disclosed herein. For purpose of clarity, details relating to technical material that is known in the technical fields related to the invention have not been described in detail so as not to unnecessarily obscure the present invention.

The acoustic echo canceling communications handset or headset is achieved with the use of an acoustic stray-field canceling receiver. The acoustic stray field canceling receiver is constructed to produce acoustic outputs at two ports, the acoustic centers of which are located in relative proximity to each other and to the user's ear when the communications device is worn by the user. The two acoustic output ports are driven and tuned such that when the headset is worn by the user, the stray field is minimized in that the acoustic power radiated from each port to the far field is substantially equal and the combined acoustic power radiated from both ports to the far field is substantially less than that of either port acting alone over a wide frequency range to thereby provide improved acoustic echo cancellation. If, for example, the acoustic loading on the two ports are nearly identical, this condition may be achieved by two identically tuned ports being driven out of phase and with equal volume velocity. The two ports may be driven by a single driver or by separate drivers as will be described below with reference to the exemplary receivers shown in FIGS. 3-8.

Figure 3A:
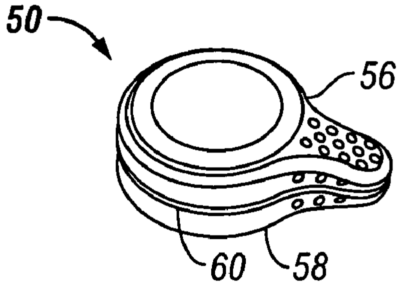
FIG. 3A is an exploded isometric view of an exemplary acoustic echo canceling headset receiver employing two drivers.
Figure 3B:
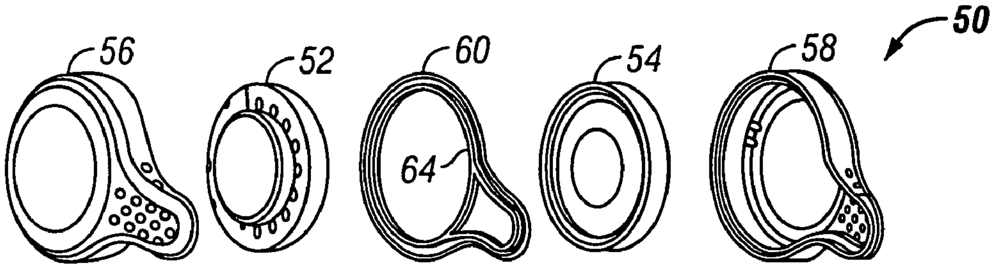
FIG. 3B is an exploded isometric view of the exemplary acoustic echo canceling headset receiver of FIG. 3A.
Figure 3C:
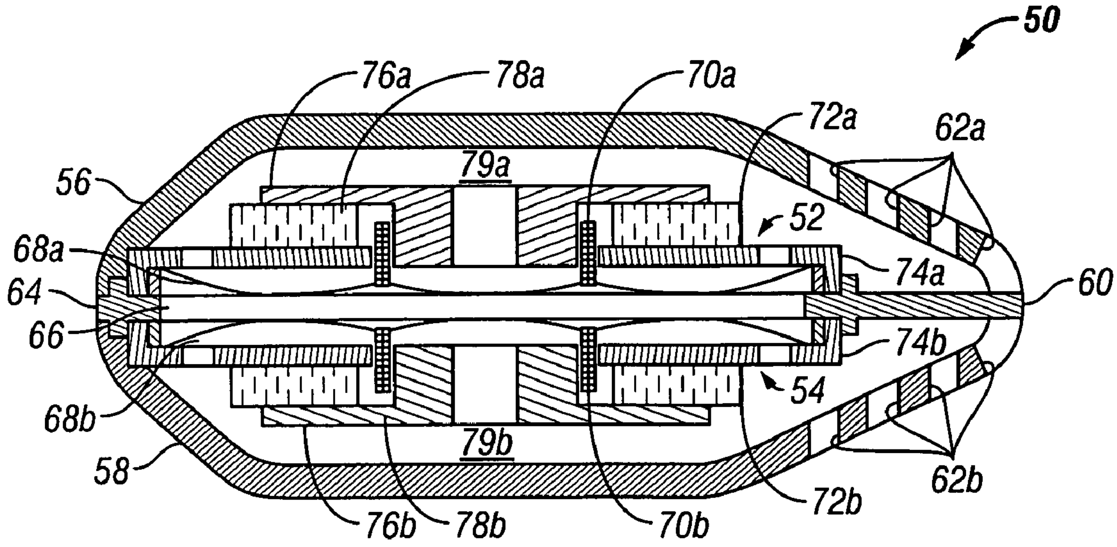
FIG. 3C is a cross-sectional view of the exemplary acoustic echo canceling headset receiver of FIG. 3A.

FIGS. 3A-3C are an isometric, an exploded isometric view, and a cross-sectional view, respectively, of an exemplary acoustic echo canceling headset receiver 50 employing two symmetrically arranged drivers 52, 54. The receiver 50 includes outer casings 56, 58 for enclosing the two drivers 52, 54 separated by a spacer 60. The outer casings 56, 58 define two ports 62*a*, 62*b*, respectively. In the embodiment shown, each port includes four port openings. It is to be understood that a port may refer to a single opening or a cluster of any suitable number of openings operating in unison as a single acoustic output terminal of an electro-acoustic transducer. Although the outer casings 56, 58 are shown as separate components, the outer casings 56, 58 may be integrally formed.

Figure 1:
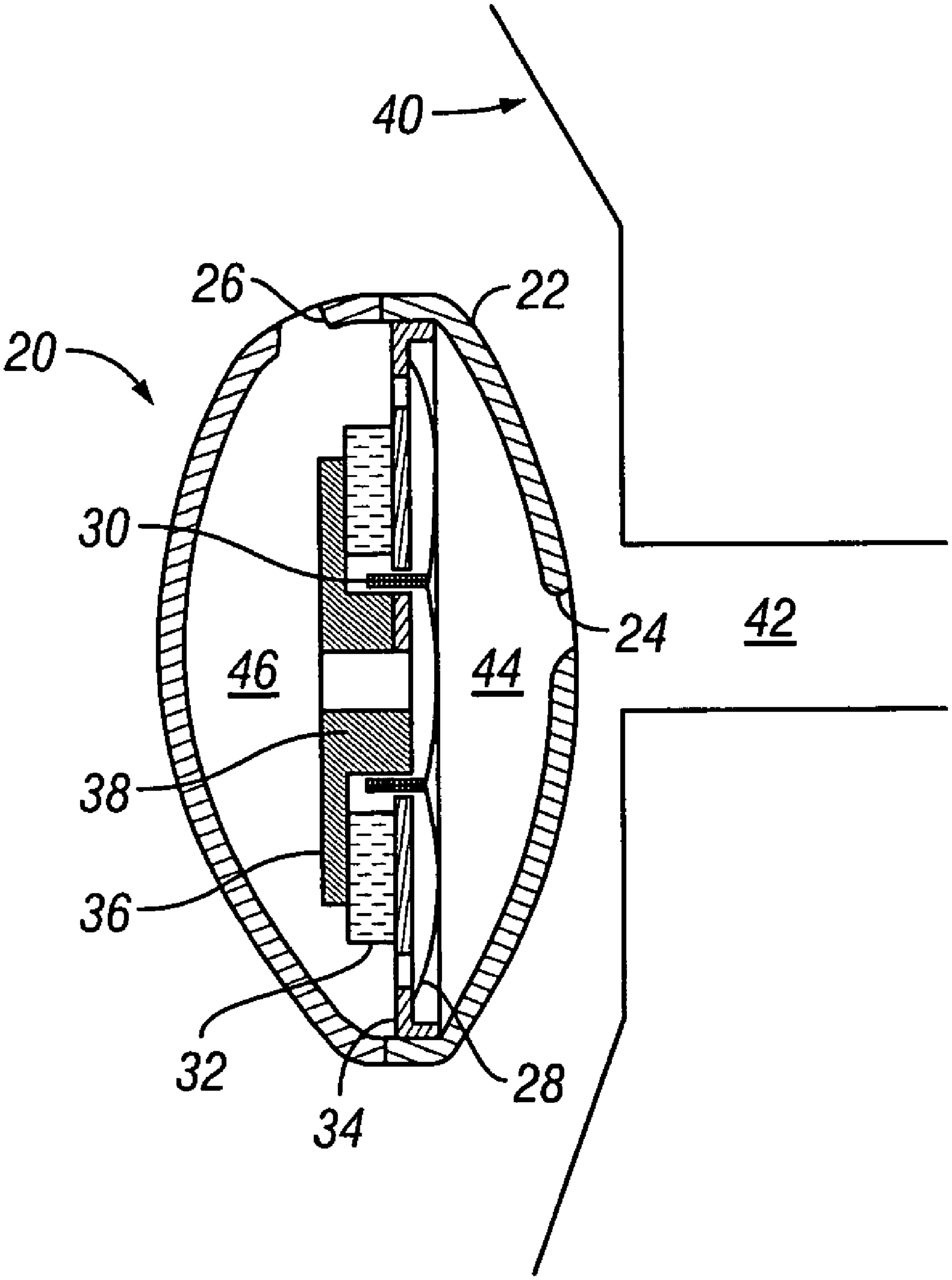
FIG. 1 (Prior Art)
FIG. 1 is a cross-sectional view of an exemplary conventional headset receiver shown in relation to a user's ear.

Each of the drivers 52, 54 may be similar to the driver for the conventional headset receiver shown in and described above with reference to FIG. 1. Referring again to FIGS. 3A-3C, each driver 52, 54 includes a voice coil 70*a*, 70*b*, a magnet 72*a*, 72*b*, a front plate 74*a*, 74*b*, a back plate 76*a*, 76*b*, and a pole piece 78*a*, 78*b*, respectively. The spacer 60 defines an opening 64 therethrough such that an acoustically sealed volume or space 66 containing a small volume of air is defined between the two diaphragms 68*a*, 68*b*. Preferably, the height of the spacer opening 64 is sufficiently large to prevent the diaphragms 68*a*, 68*b* from contacting each other when they are driven while small enough such that the air volume in the space 66 is minimized or otherwise sufficiently small so that the stiffness of air volume 66 provides a feedback mechanism to maintain the diaphragms 68*a*, 68*b* locked in amplitude and phase, i.e., to maintain constant amplitude and phase relationship between the two volume velocities for the two ports 62*a*, 62*b*. The diaphragms 68*a*, 68*b* in the embodiment shown in FIGS. 3A-3C vibrate or move together in the same direction such that a relatively constant volume in the volume 66 between the diaphragms 68*a*, 68*b* is maintained. Optionally, a microphone in the volume 66 may be utilized for electronic active control methods such as a negative feedback loop to maintain zero acoustic pressure in volume 66.

As is evident, the drivers 52, 54 are preferably identical and symmetrically positioned relative to each other. In addition, the acoustic output ports 62*a*, 62*b* are symmetrically arranged with minimum length and acoustically coupled to symmetrically arranged acoustic cavities 79*a*, 79*b* of minimum volume. The dielectric distance between the ports 62*a*, 62*b* and the current carrying metal components, namely the voice coils 70*a*, 70*b* and electrical terminals, are maximized while overall dimensions of the receiver 50 are minimized.

Figure 4A:
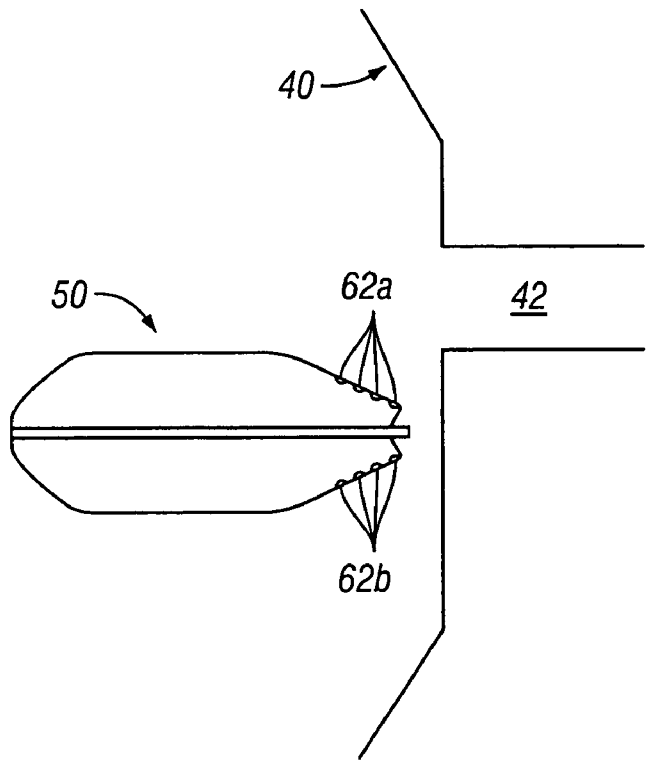
FIGS. 4A and 4B are schematics illustrating a top and a rear view, respectively, of the exemplary acoustic echo canceling headset receiver of FIGS. 3A-3C positioned relative to a user's ear.
Figure 4B:
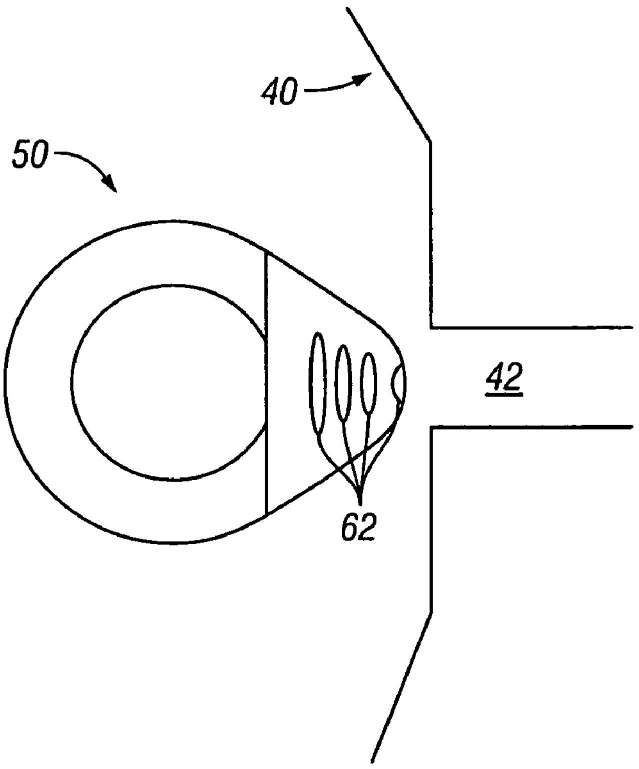

FIGS. 4A and 4B are schematics illustrating a top and a rear view, respectively, of the exemplary acoustic echo canceling headset receiver 50 of FIGS. 3A-3C positioned relative to the user's ear 40 and ear canal 42. As shown in the top view of FIG. 4A, the receiver 50 is positioned horizontally skewed or off-centered relative to the ear canal 42 such that the ports 62*a*, 62*b* are both in close proximity to but not equidistant to the ear canal 42. In the rear view of FIG. 4B, the receiver 50 is positioned to be generally centered vertically relative to the ear canal 42. FIGS. 4A and 4B merely show an exemplary position of the receiver 50 relative to the user's ear 40 to illustrate that the ports 62*a*, 62*b* are ideally close to but not equidistant from the ear canal 42. Any other suitable positioning of the receiver 50 relative to the user's user 40 and ear canal 42 may be employed.

Principles of Operation of the Acoustic Echo Canceling Headset Receiver

The various features of the acoustic stray-field canceling receiver 50 provide advantages over conventional headset receivers. A general introduction to the principles of operation for both the conventional headset receiver (for example, that shown in FIG. 1) and the acoustic echo canceling headset receiver 50 will now be described.

Simple Source and Baffle Effect. The operation of the acoustic echo canceling headset receiver 50 is generally described using an analogy to acoustic sources known as simple sources. A simple source is a source of finite size that can be considered the acoustic equivalent of a theoretical point source. In the absence of acoustically reflecting surfaces, a simple source at a given frequency creates a sound field in which the acoustic pressure in the far field is directly proportion to the volume velocity of the source and inversely proportional to the distance from the source. However, when the simple source is located a distance d from a planar surface, the acoustic pressure in the far field is equal to the sum of the combined acoustic pressures contributed by the simple source itself and an image source that appears on the far side of the surface a distance d behind the surface, analogous to a mirror image of the simple source itself. The image source has the same magnitude and phase as the simple source. As the distance d between the simple source and the planar surfaces approaches zero such that the simple source is located on the planar surface, the simple source and its image converge. In the far field, the sound pressure from the converged simple source and its image is twice that which would be produced by the simple source acting alone. This increase in sound pressure due to the presence of a surface is referred to as the baffle effect.

Dipole. A dipole is formed with two out-of-phase simple sources of equal volume velocity separated from each other by a small distance. When the separation distance between the two out-of-phase sources of the dipole decreases, the sound power from the dipole becomes smaller because the sound powers from the two out-of-phase simple sources achieve a more complete cancellation. Thus, as the separation distance between the dipole sources approaches zero, the sound power radiated into the far field approaches zero.

Front and Rear Ports of a Receiver as Dipole Sources with Baffle Effect. The receiver module of a conventional headset has a front port and often also a rear port. Each port approximates a simple source. In conventional headsets, the front and rear ports have the same volume velocity and are out of phase at low frequencies. Thus, in a free field and at low frequencies, the front and rear ports of a conventional headset behave as dipole sources. However, when the conventional headset is not in a free field but is worn by a user, the front port benefits more than the rear port from the baffle effect caused by the user's ear and head acting as a reflecting surface as the front port is closer to the ear and head of the user. As a result, in the far field, the sound pressure contributed by the rear port (and its image source) is insufficient to cancel the sound pressure contributed by the front port (and its image source) even if the volume velocities of the front and rear ports were of equal magnitude and opposite phase. The baffle effect is one reason that the HCLw of conventional headsets is compromised, i.e., decreased.

In contrast, the acoustic echo canceling receiver 50 is constructed such that the two ports 62*a*, 62*b* are disposed in relatively close proximity to each other, generally separated by, for example, no more than approximately 1 cm, and in particular, typically less than the diameter of the headphone driver. In addition, the ports 62*a*, 62*b* are disposed so that when the receiver is worn by the user both ports 62*a*, 62*b* are adjacent to the entrance to the ear canal of the user. With the ports 62*a*, 62*b* near each other and close to the ear when worn, both ports 62*a*, 62*b* benefit approximately equally from the baffle effect caused by the user's ear and head acting as reflecting surfaces.

Because both ports 62*a*, 62*b* benefit approximately equally from the baffle effect, the sound pressure contributed by one port and its image source better cancels the sound pressure contributed by the other port and its image source in the far field when the volume velocities of the ports are of equal magnitude and opposite phase. Furthermore, the small separation distance between the ports 62*a*, 62*b* acting as dipole sources also contributes to the decrease in sound power being radiated into the far field.

Conventional Headset with Single Diaphragm and Effect of Resonance. Another reason that the HCLw of conventional headsets is compromised is that the front and rear ports of conventional headsets driven by the same diaphragm with equal magnitude and opposite phase have different resonance frequencies. In particular, the volume velocities for the front and rear ports are of equal magnitude and out of phase only at low frequencies. At mid-to-high frequencies, the magnitude and phase of the volume velocity of each port are affected not only by the volume velocity of the diaphragm but also by the port resonance that occurs between the acoustic mass of the port and the acoustic compliance of the associated acoustic cavity. In conventional headsets, this port resonance generally occurs at different frequencies for the front and rear ports, causing changes in relative amplitude and phase. At frequencies higher than the port resonance frequency, each port moves out of phase with the diaphragm that drives it. Thus, when the diaphragm vibrates at a frequency that is between the resonance frequencies of the two ports, the volume velocities of the two ports on opposite sides of the diaphragm are not out of phase and their magnitudes are not equal. In conventional headsets with ported rear cavities, this condition usually occurs between 1.5 kHz and 4 kHz where the far field output is significantly higher than it is at low frequencies. Thus, the difference in port resonance frequencies also causes a decrease in the HCLw.

The acoustic echo canceling headset receiver 50 resolves this issue by providing two separately driven diaphragms. With such a configuration, the two ports 62*a*, 62*b* can be driven and tuned such that their volume velocities are of substantially equal magnitude and opposite phase over the frequency range of interest, typically a wide frequency range, preferably including the entire audible range or between 300 Hz and 4 kHz for telephone applications. The two diaphragms 68*a*, 68*b* vibrating together and the drivers 52, 54 being symmetrically arranged facilitate in driving and tuning the ports 62*a*, 62*b* with volume velocities that are equal in magnitude and opposite in phase up to the highest frequencies possible.

Proximity Effect. The acoustic intensity for a simple source is governed by the inverse square law where the acoustic intensity is inversely proportional to the square of the distance between the simple source and the observation point. Acoustic pressure is proportional to the square root of acoustic intensity and is inversely proportional to distance. For a pair of simple sources that combine to form a dipole, the sound pressure in the far field from one simple source partially cancels that from the other so that along any radial axis, the inverse square law applies to the dipole as well. In the vicinity of the dipole, however, the sound pressure from the farther simple source of the dipole does not have sufficient amplitude to cancel the sound pressure from the closer simple source of the dipole. Thus, in the near field, the sound pressure from a dipole source is greater than suggested by the inverse square law. This phenomenon, known as the proximity effect, applies not only to dipole sources but also to other clusters of simple sources.

The acoustic echo canceling receiver 50 takes advantage of the proximity effect by locating the two acoustic ports 62*a*, 62*b* in the vicinity of but not equidistant from the entrance to the ear canal such that the proximity effect takes place at the entrance to the ear canal but not at the transmit microphone. In other words, the proximity effect is generally limited to near the entrance to the ear canal when the receiver 50 is worn by the user. Thus, the ratio of sound pressure at the ear drum to that at the transmit microphone is greater than is possible with conventional headsets having either sealed, open, or ported rear cavities.

Input Equalization. An acoustic echo canceling receiver 50 constructed to maximize RTCLw as described above may not achieve a favorable frequency response at the ear drum of the user. This drawback can be addressed by equalizing the input signal as necessary. Input equalization generally does not affect RTCLw (or the echo level sent to the far end) because increasing the input in a particular frequency band results in increasing HCLw and simultaneously decreasing RRLR (loss) in that frequency band. A decrease in RRLR (loss), in return, results in less overall amplification required for the received signal. RTCLw is related to HCLw and RRLR as shown in equation (1):

$$RTCLw = HCLw - RRLR - RSLR + 8 \quad (1)$$

It should also be noted, however, that HCLw, RRLR, and RSLR have different frequency weightings, and hence, a higher RTCLw can be achieved by having a favorable combination of receive, transmit, and echo frequency response curves.

Relative source equalization. In the vicinity of the entrance to the ear canal, the sound leaving a pair of simple sources is not free to expand but rather is affected by nearby boundaries including the user's ear and the face plate of the receiver. In this enclosed environment, the relationships among port spacing, port phasing, proximity effect, and far field sound pressure do not accurately follow theoretical relationships that apply to free field radiation. Consequently, with a given headset geometry, optimum performance may be achieved not when two ports are exactly of equal magnitude and opposite phase but rather when the two ports have a particular magnitude and phase relationship relative to each other. This optimization may be achieved by acoustically detuning the cavities and ports and/or by driving each port with a separate driver and equalizing one simple source relative to the other. For example, the magnitude and phase of the volume velocities of both ports may be adjusted by equalizing for minimum sound pressure at the microphone and maximum sound pressure at the entrance to the ear canal over a wide frequency range when the headset is worn by the user. This relative equalization is separate from and may be applied in addition to an input equalization for desired frequency response at the ear drum.

Noise Canceling Microphones. When the transmit microphone is responsive to sound pressure gradient, such as in the case of a bi-directional or cardioid noise canceling microphone, aligning the microphone's sensitive axis towards the user's mouth results in increased signal-to-ambient-noise-ratio in the transmit channel especially in a diffuse field noise environment. This phenomenon is referred to as transmit noise cancellation. When such microphones are used, maximizing cancellation of the pressure gradient rather than the sound pressure in the direction of the sensitive axis of the microphone maximizes echo path loss. Where each port of the headset receiver is driven by a separate driver, equalizing one driver relative to the other results in an alteration of the polar pattern of the headset receiver so as to minimize the response of a given microphone in a given orientation, rather than the sound pressure at the microphone location.

Figure 2:
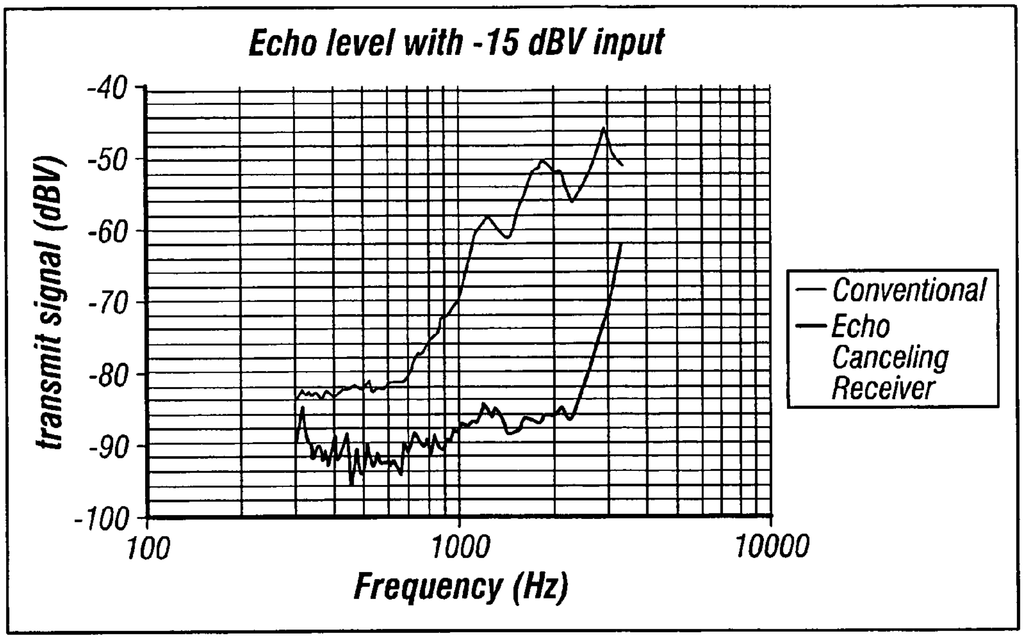
FIG. 2 is a graph illustrating the echo frequency responses of an exemplary boomless headset with an echo-canceling receiver and with a receiver of a conventional lightweight communications headset having a rear port.

As an example, FIG. 2 is a graph comparing the echo frequency response of a typical conventional lightweight communications headset and that of one with an echo-canceling receiver as described herein. Note that with the conventional receiver (as represented by the upper curve), the echo frequency response is relatively flat up to approximately 700 Hz, whereas with the echo-canceling receiver (as represented by the lower curve) the echo frequency response is relatively flat up to approximately 2000 Hz. As another example, an RTCLw of 26 dB is measured with a "boomless" headset having an echo-canceling receiver. In contrast, a "boomless" headset with the receiver of a conventional headset, the RTCLw is only 6 dB. With various experimental devices, it is demonstrated that for a given microphone location, an increase of 15 to 30 dB in RTCLw can be expected with the echo-canceling receiver built and operated as described herein.

Application of the Principles of Operation of Acoustic Echo Canceling Headset Receiver Some of the principles of operation for both the conventional headset receiver and the acoustic echo canceling headset receiver having been presented, the application of the principles of operation will now be described.

Displacement Source. As noted above, a typical dynamic driver has a diaphragm connected to a voice coil immersed in a magnetic field. An AC input signal to the voice coil causes the diaphragm to vibrate. Each half-cycle of the vibration displaces a volume of air and each face of a vibrating diaphragm is associated with a displacement source. At sufficiently low frequencies, acoustic energy radiates from the displacement source in the form of concentric, spherical waves, the common center of which is the acoustic center of the source.

Although a driver may be constructed with a cover in front of the diaphragm with an array of holes in the cover, the displacement source associated with the front face of the diaphragm is typically the diaphragm itself and thus its acoustic center coincides with the geometric center of the diaphragm. However, the same is generally not the case for the rear face of the diaphragm.

Effect of Motor Structure and Frame. Generally, the rear face of the diaphragm is at least part obscured from the surrounding medium by a motor structure of the driver and a frame or basket. Acoustic energy leaves the rear face of the diaphragm through openings provided in the frame (see for example driver 52 in FIG. 3B). An acoustic cavity is formed between these openings in the frame and the diaphragm. The vibration of the diaphragm modulates the volume of the acoustic cavity causing air columns contained in the openings to vibrate. These vibrating air columns collectively form a displacement source in the form of an array. The acoustic center of the array source coincides with the geometric center of the collection of the constituent sources. For example, in FIG. 3B, the acoustic center of the displacement source associated with the rear face of the diaphragm lies not on the diaphragm but in the plane of the sound emitting holes in the frame. Furthermore, because the holes are not symmetrically arranged, the acoustic center of the resulting displacement source is offset from a central axis of the driver.

The acoustic cavity between the diaphragm and the holes in the frame has an acoustic compliance and the air columns contained in the holes collectively have an acoustic mass. As a result of a resonance that takes place between the acoustic compliance of the acoustic cavity and the acoustic mass of the holes in the frame, the volume velocity of the displacement source in the back of the driver is not necessarily the same as that of the rear face of the diaphragm. At each cycle of the vibration, the air in the acoustic cavity is compressed and rarified. In addition, the portion of the diaphragm inside the voice coil diameter is not directly connected to the same acoustic cavity that the outer portion of the diaphragm is connected to. Therefore, the displacement source associated with the rear of the driver has a frequency-dependent magnitude and phase relationship with respect to the displacement source associated with the front of the driver. Thus, ordinarily the front and rear ports of a personal listening device are driven with equal magnitude and opposite phase only at low frequencies. In addition, they are ordinarily tuned to different frequencies, as explained below.

Port Tuning and Effect of Receiver Housing. When a driver is used in a listening device, the displacement source associated with each side of a driver is generally not in direct contact with the acoustic medium (air). Rather, it is acoustically connected to an acoustic output port. The output port is an opening in the receiver housing, and has an acoustic mass. An acoustic cavity, having an acoustic compliance, is formed between the displacement source and the acoustic port. At a particular frequency depending on the volume of the cavity and the area and length of the port, a resonance occurs between the acoustic mass of the port and the acoustic compliance of the cavity. Selecting these design parameters to control the frequency of resonance is called tuning the port. At frequencies sufficiently less than the port tuning frequency, the volume velocity of the port and the volume velocity of the associated displacement source are of equal magnitude and phase. At frequencies sufficiently greater than the tuning frequency, the volume velocity of the port and the volume velocity of the associated displacement source are of opposite phase, and the amplitude of the volume velocity of the port is substantially less than that of the displacement source. In other words, due to the inertia of the port, at high frequencies most of the displacement results merely in compressing and rarifying the air in the acoustic cavity.

Personal Listening and Communication Devices. A personal listening device generally refers to a device that is held or worn next to a user's ear to receive an audio signal. Personal listening devices are distinguished from general listening devices in that their sound emitting parts are positioned next to the car so as to deliver the received signal only to a particular user. A personal listening device may be the receiver or listening portion of a personal communication device such as stereo headphones, telephone headset or handset. In contrast, loudspeakers or radio receivers are listening devices that do not fall within the personal listening category.

A personal listening device may be incorporated in a personal communication device. A personal communication device generally refers to a receiving and transmitting apparatus that is held or worn with the receiving portion next to the ear to receive and transmit communication signals. Telephone handsets and aviation headsets are examples of personal communication devices whereas speakerphones and intercom devices do not fall into the personal communication category.

Near and Far Fields. The sound field of a sound source can be thought of as having two regions: near field and far field. In the far field the sound pressure usually decreases linearly with distance from the acoustic center of the source if two conditions are met. First, the distance from the source is large relative to the size of the displacement source. Second, the distance from the source is large relative to ⅙ of the wavelength being emitted. The size factor is usually taken to be larger than 3 to 10.

Constructive and Destructive Interferences. The contribution of sound radiating from the rear port may be constructive (positive) or destructive (negative) with respect to that from the front port. Ordinarily, at low frequencies, the sound radiated from the rear port would cancel the sound radiated from the front port (destructive interference). Therefore, conventional personal listening devices are constructed such that only the front port is near the entrance to the ear canal. Such an arrangement maximizes the electro-acoustic efficiency and results in a desirable frequency response at the ear. The rear port is conventionally in the far side of the driver and away from the ear and therefore its out-of-phase acoustic output does not significantly contribute to the sound field at the entrance to the ear canal, i.e., no interference.

However, in personal communication devices with conventional personal listening devices, the acoustic output of the rear port makes a significant contribution to the sound field at the transmit microphone. In conventional personal communication devices, the rear port acts to cancel the output of the front port (destructive interference) at low frequencies, but acts to enforce (constructive interference) at high frequencies.

A personal communication device with the echo canceling receiver as described herein generally provides the destructive interference in the far field and particularly at the location of the transmit microphone up to high frequencies. In the particular, sound emitted from the rear port of the echo canceling receiver acts to cancel the sound emitted from the front port (destructive interference) up to higher frequencies than conventional personal communication devices. The destructive interference is achieved by reducing port spacing and controlling the magnitude and phase relationship between the ports to achieve destructive interference at the microphone. Although the destructive interference generally reduces the sound pressure at the entrance to the ear canal relative to the conventional receiver, the interference at the entrance to the ear canal (which is relatively close to the source) is less destructive than the interference at the microphone (which is relatively far from the source) when the echo canceling receiver is constructed and operated according to principles described herein. The difference in the level of the destructive interference between the near field and the far field results from a phenomenon analogous to the proximity effect that characterizes close talking microphones. Therefore, the echo canceling receiver may be analogized to a "close talking receiver."

Proximity Effect. In acoustics, although the tenn proximity effect generally refers to microphones, the term as utilized herein generally involves its equivalent in sound sources. At distances sufficiently close to one source of a composite sound source having two simple sources of opposite phase separated by a small distance, the sound pressure is greater than that from a simple source having the same output in the far field.

For a given receive sensitivity, the relative strength of the sound field at the entrance to the ear canal compared to that at the transmit microphone (receive proximity effect) with the echo canceling receiver results in greater echo path loss compared with conventional personal communication devices.

Acoustic Distance or Separation. The acoustic distance between two points is the minimum distance that airborne sound waves travel from one point to another. When two sound sources are separated only by a free air path, the acoustic distance between the sources is simply a straight line connecting their acoustic centers. When two sound sources are located on a curved surface of a housing, as is often the case for front and rear ports of a personal listening device, the acoustic distance between the sources is measured on the curved surface of the housing.

Additional Examples of Acoustic Echo Canceling Headset Receiver

Figure 5:
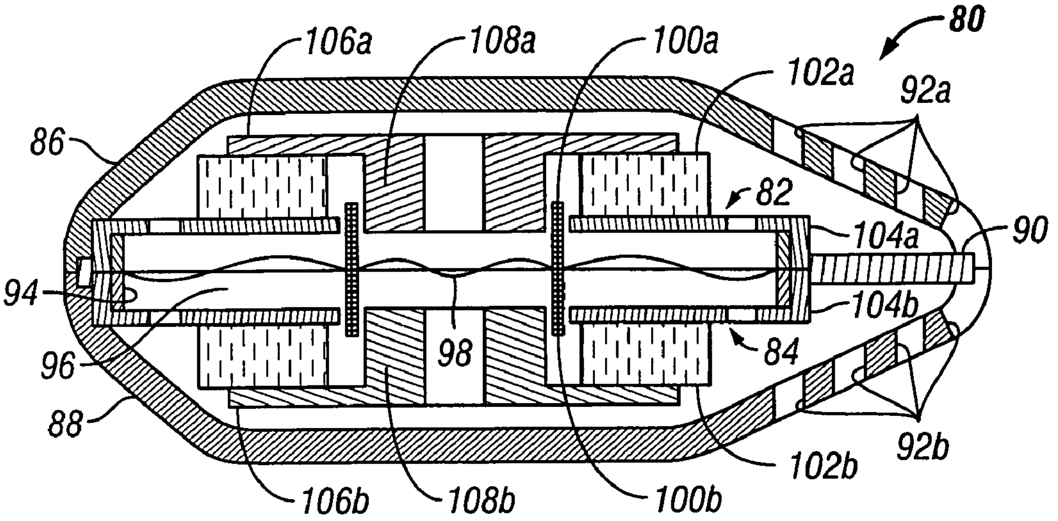
FIG. 5 is a cross-sectional view of an exemplary acoustic echo canceling headset receiver with a single diaphragm between two symmetrically arranged motor structures.

FIG. 5 is a cross-sectional view of another exemplary acoustic echo canceling headset receiver 80. In contrast to the acoustic echo canceling headset receiver 50 of FIGS. 3A-4B with two separately driven diaphragms, the acoustic echo canceling headset receiver 80 has two symmetrically arranged motor structures 82, 84 driving a single diaphragm 98 disposed between the motor structures 82, 84. The receiver 80 includes outer casings 86, 88 for enclosing the two drivers 82, 84 separated by a spacer 90. The outer casings 86, 88 define two ports 92*a*, 92*b*, respectively. Similar to the embodiment shown in FIGS. 3A-4B, each port includes four port openings. Each of the motor structures 82, 84 includes a voice coil 100*a*, 100*b*, a magnet 102*a*, 102*b*, a front plate 104*a*, 104*b*, a back plate 106*a*, 106*b*, and a pole piece 108*a*, 108*b*, respectively. The spacer 90 defines an opening 94 therethrough such that a space 96 containing a small volume of air is defined between the motor structures 82, 84. The diaphragm 98 is centrally located within the space 96 between the two motor structures 82, 84.

The two ports 92*a*, 92*b* and acoustic cavities 109*a*, 109*b* corresponding to the two ports 92*a*, 92*b* are identical and symmetrically arranged. Such symmetry ensures that the port resonance frequencies are the same for both ports 92*a*, 92*b*. Thus, ports 92*a*, 92*b* have volume velocities that are equal in magnitude and opposite in phase over a wide frequency range. The symmetry may be achieved with an active motor structure on each side of the diaphragm, as shown in FIG. 5. Alternatively, the symmetry may be achieve by providing an active motor structure on one side of the diaphragm and a passive structure that generates no motor force but ensures that the acoustic circuit inserted between one side of the diaphragm and the corresponding acoustic port is identical to the acoustic circuit inserted between the other side of the diaphragm and the corresponding port.

In addition, FIG. 5 illustrates an exemplary embodiment in which the dielectric distance between the ports 92*a*, 92*b* and current carrying metal components, namely the voice coils 100*a*, 100*b* and electrical terminals, are maximized while overall dimensions of the receiver 80 are minimized.

Figure 6A:
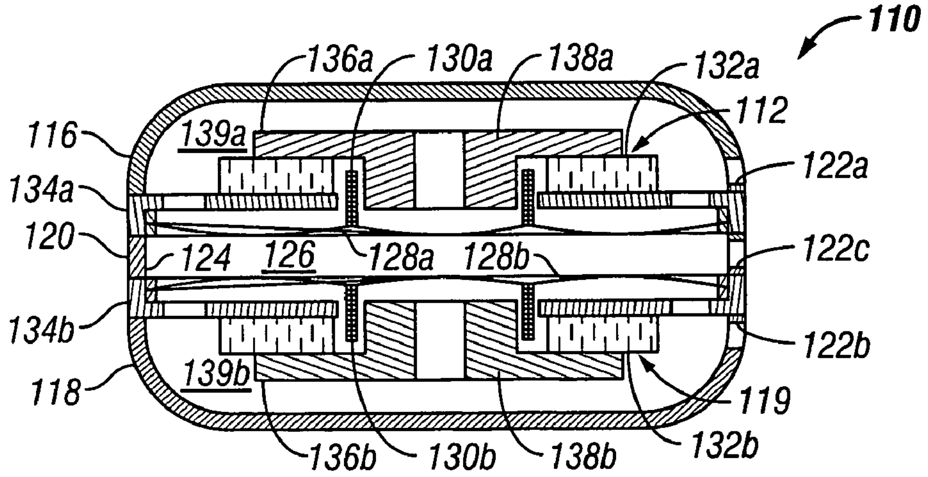
FIGS. 6A and 6B are a cross-sectional and a side view, respectively, of an exemplary acoustic echo canceling headset receiver with two drivers acoustically coupled to three ports.
Figure 6B:
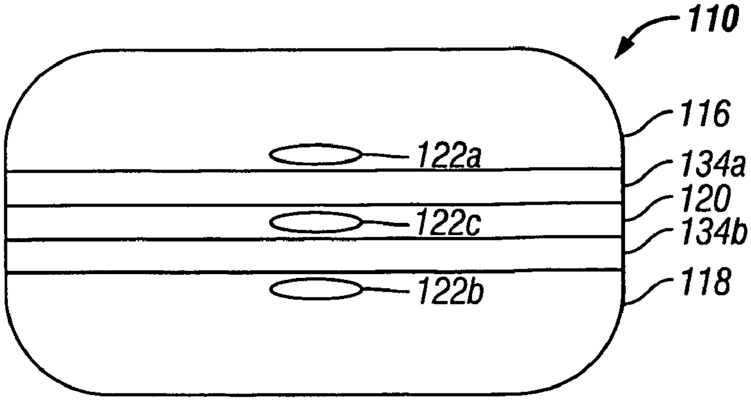

FIGS. 6A and 6B are a cross-sectional and a side view, respectively, of an exemplary acoustic echo canceling headset receiver 110 with two drivers 112, 114 acoustically coupled to a tripole sound source, i.e., three ports 122*a*, 122*b*, 122*c*. Each of the two distal ports 122*a*, 122*b* preferably produces half the volume velocity of the medial port 122*c*, and that the volume velocity produced at ports 122*a* and 122*b* is opposite in phase as compared to the remaining middle port 122*c*. Each of the three ports 122*a*, 122*b*, 122*c* can be located in any suitable geometric arrangement with respect to each other. Preferably, in a telephone headset, the opening with the largest volume velocity, i.e., port 122*c* will be closest to the entrance to the ear canal so as to produce the largest possible sound pressure at the ear canal. However, the total acoustic output of the receiver 110 in the far field is still minimized over a wide range of frequencies by having all acoustic ports 122 whose combined volume velocity is virtually zero, located as closely relative to each other as practical. The receiver 110 is merely one embodiment in which one of the acoustic ports is subdivided into two separate ports. However, it is to be understood that either or both of the acoustic ports may be subdivided into any suitable number of ports and/or be arranged in any suitable geometric pattern. Alternately, the three ports 122*a*, 122*b* and 122*c* can be thought of as a linear quadrupole in which two like-phase poles converge into a single opening 122*c*.

The receiver 110 includes outer casings 116, 118 for enclosing the two drivers 112, 114 separated by a spacer 120. The two drivers 112, 114 are identical and symmetrically arranged relative to a plane of symmetry coincident with the spacer 120. Each of the drivers 112, 114 includes a voice coil 130*a*, 130*b*, a magnet 132*a*, 132*b*, a front plate 134*a*, 134*b*, a back plate 136*a*, 136*b*, and a pole piece 138*a*, 138*b*, respectively. The spacer 120 defines an opening 124 therethrough such that a space 126 containing a small volume of air is defined between the motor structures 82, 84. The diaphragm 98 is centrally located within the space 96. Ports 122*a*, 122*b* are driven and tuned such that their combined volume velocities are of substantially equal magnitude and opposite phase when compared to port 122*c* over the frequency range of interest, e.g., 300 Hz to 4 kHz.

The diaphragms 128*a*, 128*b* are driven with equal volume velocity and in-phase, i.e., moving towards and away from each other. In a preferred embodiment, the volume 126 between the diaphragms 128*a*, 128*b* and the net volumes of acoustic cavities 139*a*, 139*b* on the other sides of the diaphragms are all equal, as are the acoustic masses of the three ports 122*a*, 122*b*, 122*c*. As a result, over a wide frequency range, the middle port 122*c* has twice the volume velocity of each of ports 122*a*, 122*b* and the outer ports 122*a*, 122*b* are in phase with each other and out of phase with the middle ports 122*c*, and the total instantaneous volume velocity is zero.

The receiver 110 is symmetrically arranged with respect to a symmetry plane coincident with the spacer 120. Such symmetry ensures that the port resonance frequencies are the same for ports 122*a*, 122*b*. Thus, ports 122*a*, 122*b* have volume velocities that are equal in magnitude and in phase over a wide frequency range.

Figure 7:
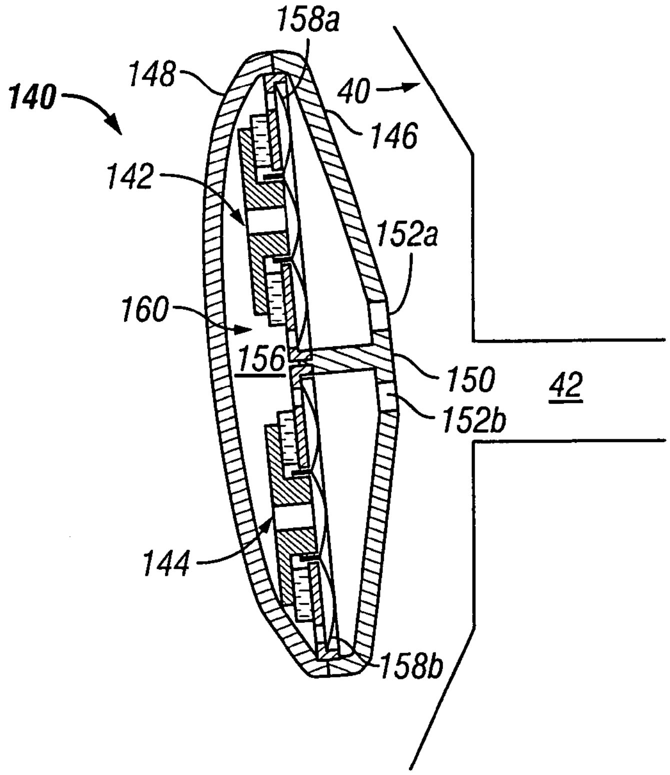
FIG. 7 is a cross-sectional view of an exemplary acoustic echo canceling headset receiver with two out-of-phase drivers and a sealed rear cavity to help maintain the two drives phase-locked.

FIG. 7 is a cross-sectional view of an exemplary acoustic echo canceling headset receiver 140 with two out-of-phase drivers 142, 144. The receiver 140 includes outer casings 146, 148 for enclosing the two drivers 142, 144. The outer casing 148 and the two out-of-phase drivers 142, 144 form a sealed rear cavity 156 to help maintain the two drivers 142, 144 locked in amplitude and phase. The two drivers 142, 144 are identical. The outer casing 146 provides two ports 152*a*, 152*b*. Ports 152*a*, 152*b* are driven and tuned such that their volume velocities are of substantially equal magnitude and opposite phase over a wide frequency range, e.g., the entire frequency range for telephony.

Preferably, sealed rear cavity 156 is small enough such that the air volume in the cavity 156 is minimized or otherwise sufficiently small so that the stiffness of air in the cavity 156 provides a feedback mechanism to maintain the diaphragms 158*a*, 158*b* locked in amplitude and phase, i.e., to maintain a constant phase relationship between the two volume velocities. It is noted that the diaphragms 158*a*, 158*b* in the embodiment shown in FIG. 7 vibrate or move together in the opposite directions such that a relatively constant volume in the cavity 156 is maintained.

Optionally, a microphone 160 in the cavity 156 may be utilized for electronic active control methods such as a negative feedback loop. For example, using such a microphone in a negative feedback loop, one of the drivers 142 may be configured to respond to input signals while the other driver 142 is in feedback control to make the sound pressure in the acoustically sealed air volume 156 zero.

As shown, the receiver 140 may be positioned relative to the user's ear 40 such that the ports 152*a*, 152*b* are offset relative to the entrance to the ear canal 42. An optional baffle (not shown) may be provided to further enhance the proximity effect in order to produce more sound pressure at the ear canal 42. The baffle serves to better couple one port 152*b* to the ear canal 42 than the other port 152. The baffle may be provided as an extension of the spacer 150 extending outwardly from the outer casing 146 toward the ear, for example.

Figure 8:
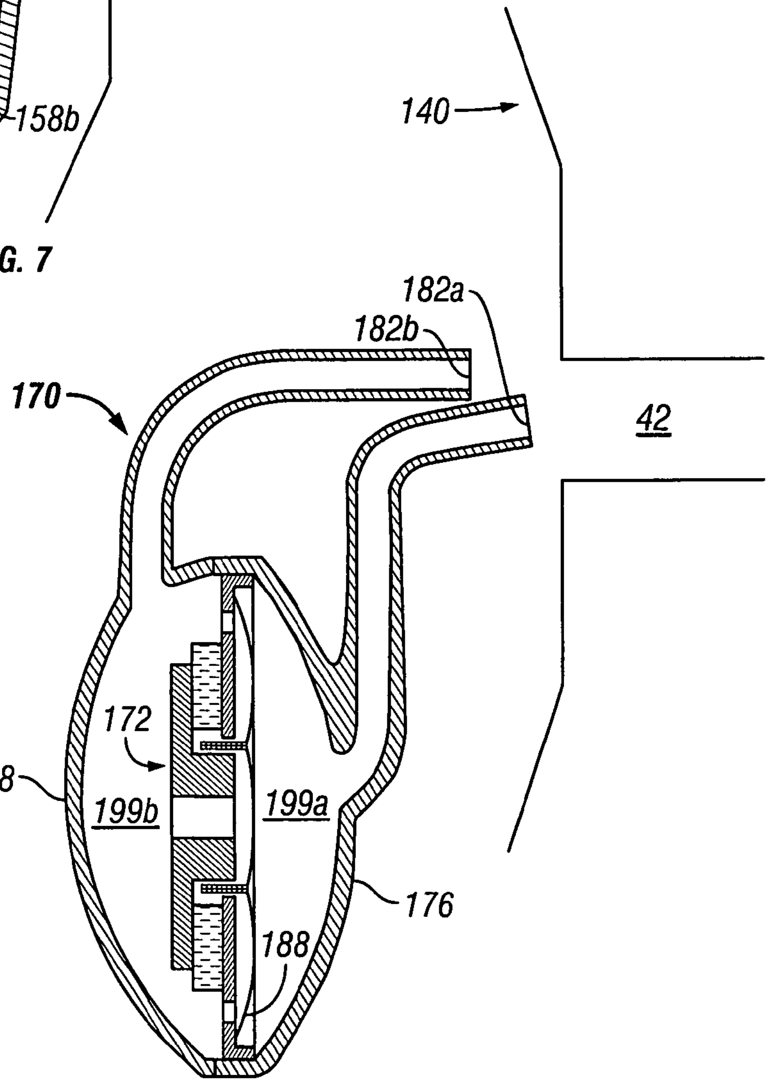
FIG. 8 is a cross-sectional view of an exemplary acoustic echo canceling headset receiver with a single driver having a single motor structure.

FIG. 8 is a cross-sectional view of an exemplary acoustic echo canceling headset receiver 170 with a diaphragm 188 driven by a single driver 172. The driver 172 is constructed such that both sides of the diaphragm 188 have the same volume velocity over a wide range of frequencies.

The receiver 170 includes outer casings 176, 178 for enclosing the driver 172. Each of the outer casings 176, 178 includes an extension that terminates in a port 182*a*, 182*b*, respectively. The driver 172 divides the cavity defined by the outer casing 148 into two acoustic cavities 199*a*, 199*b* corresponding to the two ports 182*a*, 182*b*, respectively.

Ports 182*a*, 182*b* are tuned such that their volume velocities are of substantially equal magnitude and opposite phase over a wide frequency range of interest, e.g., 300 Hz to 4 kHz. As an example, the acoustic cavities 199*a*, 199*b* have the same volume and the ports 182*a*, 182*b* have the same length and cross section; i.e., the ports are tuned to the same frequency to help maintain the outputs at the ports 182*a*, 182*b* at the same amplitude and opposite in phase regardless of frequency. However, it should be apparent that having identical port dimensions and identical volumes is not a necessary condition to tune the ports identically.

Several preferred embodiments of the acoustic echo canceling headset have been presented. However, they are merely some exemplary implementations for illustrating employing acoustic stray field cancellation and proximity effect in the receiver. As described above, the acoustic echo canceling receiver utilizes two acoustic output ports driven and tuned such that their volume velocities are substantially equal in magnitude and opposite in phase over a wide frequency range in order to minimize sound pressure in the far field (stray field) and particular at the transmit module of a headset or handset, for example. In other words, the acoustic power radiated from each port to the far field is substantially equal and the combined acoustic power radiated from both ports to the far field is substantially less than that of either port acting alone over a wide frequency range. However, due to the proximity effect, the sound pressure in the near field, i.e., at or near the entrance to the user's ear canal when worn by the user, is sufficiently large. Thus, the ratio of acoustic pressure at a near field location (e.g., at the entrance to ear canal) to acoustic pressure or pressure gradient at a second location (e.g., at the transmit module or at a location that is further away) is substantially greater than that with either port acting alone, over a wide frequency range.

While the preferred embodiments of the present invention are described and illustrated herein, it will be appreciated that they are merely illustrative and that modifications can be made to these embodiments without departing from the spirit and scope of the invention. Thus, the invention is intended to be defined only in terms of the following claims.

What is claimed is:

1. A personal communication device comprising:

a receiver module for receiving signals arriving at the personal communication device, the receiver module having:

two displacement sources that are not in phase and formed by at least one driver, each displacement source having an acoustic center, two separate acoustic cavities, each acoustic cavity corresponding to one of the displacement sources, and two acoustic output ports each having an acoustic center, each acoustic output port corresponding to one of the displacement sources and in acoustic connection therewith via the corresponding acoustic cavity such that the length of acoustic path between the acoustic centers of the two acoustic output ports is less than the distance between the acoustic center of each output port and the acoustic center of the corresponding displacement source to which the output port is acoustically connected; and a transmit module for transmitting signals from the personal communication device, wherein the output ports of the receiver module are driven and tuned such that when the communication device is worn by a person, the ratio of acoustic pressure at a first location to acoustic pressure at a second location further away from the output ports than the first location is substantially greater than that with either port acting alone over a predetermined frequency range.

2. The personal communication device of claim 1, wherein the transmit module includes an omnidirectional microphone.

3. A personal communication device, comprising:

a receiver module for receiving signals arriving at the personal communication device, the receiver module having:

two displacement sources that are not in phase and formed by at least one driver, each displacement source having an acoustic center;

two separate acoustic cavities, each acoustic cavity corresponding to one of the displacement sources, and an acoustic output port corresponding to each displacement source and in acoustic connection therewith via the corresponding acoustic cavity such that both output ports are located on a same side of a surface of at least one of the displacement sources; and a transmit module for transmitting signals from the personal communication device, wherein the output ports of the receiver module are driven and tuned such that when the communication device is worn by a person, ratio of acoustic pressure at a first location to acoustic pressure at a second location further away from the output ports than the first location is substantially greater than that with either port acting alone over a predetermined frequency range.

4. The personal communication device of claim 3, wherein the transmit module includes an omnidirectional microphone.

5. A personal communication device comprising:

a receiver module for receiving signals arriving at the personal communication device, the receiver module having:

two displacement sources that are not in phase and formed by at least one driver, each displacement source having an acoustic center;

two separate acoustic cavities, each acoustic cavity corresponding to one of the displacement sources, and two acoustic output ports each having an acoustic center, each acoustic output port corresponding to one of the displacement sources and in acoustic connection therewith via the corresponding acoustic cavity such that the length of acoustic path between the acoustic centers of the two acoustic output ports is less than the distance between the acoustic center of each output port and the acoustic center of the corresponding displacement source to which the output port is acoustically connected; and a transmit module for transmitting signals from the personal communication device, wherein the output ports of the receiver module are driven and tuned such that when the communication device is worn by a person, ratio of acoustic pressure at a first location to sound pressure gradient in a given direction at a second location further away from the output ports than the first location is substantially greater than that with either port acting alone over a predetermined frequency range.

6. The personal communication device of claim 5, wherein the transmit module includes directional microphone.

7. A personal communication device, comprising:

a receiver module for receiving signals arriving at the personal communication device, the receiver module having:

two displacement sources that are not in phase and formed by at least one driver, each displacement source having an acoustic center;

two separate acoustic cavities, each acoustic cavity corresponding to one of the displacement sources, and an acoustic output port corresponding to each displacement source and in acoustic connection therewith via the corresponding acoustic cavity such that both output ports are located on a same side of a surface of at least one of the displacement sources; and a transmit module for transmitting signals from the personal communication device, wherein the output ports of the receiver module are driven and tuned such that when the communication device is worn by a person, ratio of acoustic pressure at a first location to sound pressure gradient in a given direction at a second location further away from the output ports than the first location is substantially greater than that with either port acting alone over a predetermined frequency range.

8. The personal communication device of claim 7, wherein the transmit module includes a directional microphone.

9. A personal listening device, comprising:

two displacement sources that are not in phase and formed by at least one driver, each displacement source having an acoustic center;

two separate acoustic cavities, each acoustic cavity corresponding to one of the displacement sources; and two acoustic output ports each having an acoustic center, each acoustic output port corresponding to one of the displacement sources and in acoustic connection therewith via the corresponding acoustic cavity such that the length of acoustic path between the acoustic centers of the two acoustic output ports is less than the distance between the acoustic center of each output port and the acoustic center of the corresponding displacement source to which the output port is acoustically connected, wherein the output ports are driven and tuned such that when the personal listening device is worn by a person, acoustic power radiated from each output port to a far field is substantially equal and the combined acoustic power radiated from both ports to the far field is substantially less than that of either port acting alone over a predetermined frequency range.

10. The personal listening device of claim 9, wherein the output ports are driven by the displacement sources of substantially equal magnitude and opposite phase and tuned to substantially equal frequencies.

11. A personal listening device, comprising:

two displacement sources that are not in phase and formed by at least one driver, each displacement source having an acoustic center;

two separate acoustic cavities, each acoustic cavity corresponding to one of the displacement sources; and two acoustic output ports each having an acoustic center, each acoustic output port corresponding to one of the displacement sources and in acoustic connection therewith via the corresponding acoustic cavity such that the length of acoustic path between the acoustic centers of the two acoustic output ports is less than the distance between the acoustic center of each output port and the acoustic center of the corresponding displacement source to which the output port is acoustically connected, wherein the output ports are arranged such that when the personal listening device is worn by a user both output ports are located in the vicinity of an entrance to an ear canal of the user.

12. The personal listening device of claim 11, wherein the two ports are located such that a proximity effect occurs at the entrance to the ear canal.

13. A personal listening device, comprising:

two displacement sources that are not in phase and formed by at least one driver, each displacement source having an acoustic center;

two separate acoustic cavities, each acoustic cavity corresponding to one of the displacement sources; and two acoustic output ports, each corresponding to one of the displacement sources and in acoustic connection therewith via the corresponding acoustic cavity such that both output ports are located on a same side of a surface of at least one of the displacement sources, wherein the output ports are driven and tuned such that when the personal listening device is worn by a person, acoustic power radiated from each output port to a far field is substantially equal and the combined acoustic power radiated from both ports to the far field is substantially less than that of either port acting alone over a predetermined frequency range.

14. The personal listening device of claim 13, wherein the output ports are driven by the displacement sources of substantially equal magnitude and opposite phase and tuned to substantially equal frequencies.

15. A personal listening device, comprising:

two displacement sources that are not in phase and formed by at least one driver, each displacement source having an acoustic center;

two separate acoustic cavities, each acoustic cavity corresponding to one of the displacement sources; and two acoustic output ports, each corresponding to one of the displacement sources and in acoustic connection therewith via the corresponding acoustic cavity such that both output ports are located on a same side of a surface of at least one of the displacement sources, wherein the output ports are arranged such that when the personal listening device is worn by a user both output ports are located in the vicinity of an entrance to an ear canal of the user.

16. The personal listening device of claim 15, wherein the two ports are located such that a proximity effect occurs at the entrance to the ear canal.

* * * * *